(12) United States Patent
York (10) Patent No.: US 9,855,171 B2
(45) Date of Patent: Jan. 2, 2018

(54) SAFETY GLASSES (71) Applicant: Jeffrey S. York, White Lake, MI (US)

(72) Inventor: Jeffrey S. York, White Lake, MI (US)

(73) Assignee: 3R PRODUCTS, LLC, Overland Park, KS (US)

( * ) Notice: Subject to any disclaimer, the term of this patent is extended or adjusted under 35 U.S.C. 154(b) by 127 days.

(21) Appl. No.: 14/638,653

(22) Filed: Mar. 4, 2015

(65) Prior Publication Data
US 2016/0256326 A1 Sep. 8, 2016

(51) Int. Cl.
*A61F 9/02* (2006.01)
*A61F 11/12* (2006.01)

(52) U.S. Cl.
CPC ............ *A61F 9/029* (2013.01); *A61F 11/12* (2013.01)

(58) Field of Classification Search
CPC ........... A61F 9/029; A61F 11/08; G02C 5/143
USPC ............................................................ 2/431
See application file for complete search history.

(56) References Cited

U.S. PATENT DOCUMENTS

| | | | | | |
|---|---|---|---|---|---|
| 3,957,361 | A | * | 5/1976 | Buccicone | G02C 3/003 351/123 |
| 4,603,951 | A | * | 8/1986 | Beck | G02C 11/00 351/123 |
| 5,475,449 | A | * | 12/1995 | Pyle | A61F 11/12 181/130 |
| 5,495,303 | A | * | 2/1996 | Kolentsi | A61F 9/026 2/428 |
| 5,541,677 | A | * | 7/1996 | Huhtala | A61F 11/12 351/123 |
| 5,655,263 | A | * | 8/1997 | Stoller | G02C 3/003 24/3.3 |
| 5,664,291 | A | * | 9/1997 | Stoller | G02C 3/003 24/3.3 |
| 5,703,670 | A | | 12/1997 | Callard | |
| 5,781,272 | A | | 7/1998 | Bright et al. | |
| 5,806,526 | A | | 9/1998 | Rhoad | |
| 6,059,408 | A | * | 5/2000 | Bonacci | G02C 5/00 351/43 |
| 6,067,664 | A | | 5/2000 | Cortes | |
| 6,074,060 | A | * | 6/2000 | Bruce | A61F 9/029 351/158 |
| 6,082,855 | A | * | 7/2000 | Fleming | A61F 9/029 351/123 |
| 6,176,576 | B1 | * | 1/2001 | Green | A61F 9/029 351/111 |

(Continued)

*Primary Examiner* — Nathan Durham
*Assistant Examiner* — Anne Kozak
(74) *Attorney, Agent, or Firm* — Jason P. Webb; Pearson Butler (57) ABSTRACT

A pair of safety glasses including a pair of arms extending from opposite sides of an eye glass shield member. A terminal end of each of the arms, opposite the eye shield member, includes a near terminal region curves inwardly toward the other arm and a far terminal region, further from the eye shield member than the near terminal region, that curves outwardly and wherein the far terminal region includes a trap defined by a hole through the far terminal region in communication with a slit extending from the hole to an exterior side of the far terminal region with a protrusion extending into the hole, from an edge of the hole, near the slit. The pair of safety glasses includes an earplug lanyard coupled through each hole of the pair of arms.

18 Claims, 6 Drawing Sheets

(56) References Cited

U.S. PATENT DOCUMENTS

| | | | | |
|---|---|---|---|---|
| 6,233,345 B1 * | 5/2001 | Urwyler | | H04R 1/1033 |
| | | | | 351/123 |
| 6,340,227 B1 * | 1/2002 | Solberg | | G02C 11/00 |
| | | | | 351/123 |
| 6,950,531 B2 * | 9/2005 | Rickards | | G02C 11/10 |
| | | | | 351/41 |
| 7,011,405 B2 * | 3/2006 | Chen | | G02C 1/02 |
| | | | | 351/110 |
| 7,055,952 B2 * | 6/2006 | Fecteau | | G02C 5/00 |
| | | | | 351/122 |
| 7,213,916 B1 * | 5/2007 | Pettett | | G02C 11/00 |
| | | | | 351/123 |
| 7,556,374 B1 * | 7/2009 | Cooper | | G02C 5/143 |
| | | | | 351/112 |
| 7,559,647 B2 * | 7/2009 | Curiel | | G02C 3/003 |
| | | | | 351/103 |
| 7,641,334 B1 * | 1/2010 | Goldie | | G02C 11/00 |
| | | | | 128/864 |
| D619,637 S * | 7/2010 | Vanne | | D16/339 |
| 7,810,750 B2 * | 10/2010 | Abreu | | G02C 3/003 |
| | | | | 242/378.1 |
| D634,354 S * | 3/2011 | Schwartz | | D16/339 |
| 7,921,468 B2 * | 4/2011 | Sutton | | A61F 11/12 |
| | | | | 2/11 |
| 7,997,721 B1 * | 8/2011 | Burcham | | G02C 5/20 |
| | | | | 351/123 |
| D666,287 S * | 8/2012 | Quinlan | | D16/309 |
| 8,588,448 B1 * | 11/2013 | Rickards | | G02C 11/10 |
| | | | | 381/322 |
| 8,671,949 B2 * | 3/2014 | Oshima | | A61F 9/029 |
| | | | | 128/858 |
| 8,744,113 B1 * | 6/2014 | Rickards | | H04R 1/028 |
| | | | | 379/430 |
| 8,820,921 B1 * | 9/2014 | Lier | | G02C 5/20 |
| | | | | 351/120 |
| 8,939,769 B2 * | 1/2015 | Yoo | | H04R 25/606 |
| | | | | 434/247 |
| 9,088,848 B2 * | 7/2015 | Abreu | | G02C 3/003 |
| D743,370 S * | 11/2015 | Toelle | | D14/205 |
| 9,241,209 B2 * | 1/2016 | Toelle | | H04R 1/1058 |
| 9,351,881 B2 * | 5/2016 | Crawford | | A61F 9/029 |
| 2003/0030771 A1 * | 2/2003 | Hursey, Jr. | | A61F 11/12 |
| | | | | 351/123 |
| 2003/0193645 A1 * | 10/2003 | Gilmore | | A61F 9/029 |
| | | | | 351/158 |
| 2004/0085509 A1 * | 5/2004 | Lovelace | | A61F 9/029 |
| | | | | 351/123 |
| 2009/0165189 A1 * | 7/2009 | Purcell | | A61F 9/027 |
| | | | | 2/209 |
| 2010/0302501 A1 * | 12/2010 | Hansen | | A61F 9/029 |
| | | | | 351/158 |
| 2011/0255049 A1 * | 10/2011 | Corona | | G02C 11/00 |
| | | | | 351/123 |

* cited by examiner

SAFETY GLASSES

BACKGROUND OF THE INVENTION

Field of the Invention

The present invention relates to safety glasses, specifically safety glasses including ear protection.

Description of the Related Art

Safety glasses are worn to protect the eyes during a variety of tasks. They are made with shatter-resistant plastic lenses to protect the eye from flying debris and may shield the eyes from hazardous splatters such as blood or chemicals. There are also safety glasses for welding, which are styled like wraparound sunglasses, but with much darker lenses, for use in welding where a full sized welding helmet is inconvenient or uncomfortable. These are often called "flash goggles", because they provide protection from welding flash. Nylon frames are usually used for protection eyewear for sports because of their lightweight and flexible properties.

There are mainly four types of earplugs for hearing protection: Foam earplugs, mainly made of memory foam, which are compressed and put into the ear canal, where they expand to plug it. Silicone earplugs, which are rolled into a ball and carefully molded to fit over the external portion of the ear canal. Flanged earplugs, including most types of musicians' or 'Hi-Fi' earplugs. Custom molded earplugs, made from a mould of the wearer's ear and designed to precisely fit all ear canal shapes. Custom molded is further divided into Laboratory made and "formed in place".

Furthermore, they may be either disposable or non-disposable, with foam and hand rolled silicone ones generally being disposable or for use a relatively limited number of times. Custom molded are non-disposable and made from either acrylic, vinyl, or silicone materials. Custom molded come as either vented (for communication) or non-vented (for high noise). A variation of the traditional foam earplug is the no-roll foam earplug that uses a built-in central stem to push the foam plugs into the ears. These earplugs achieve a seal due to their tapered shape, rather than expansion after being rolled. Ear plugs are especially useful to people exposed to excessively noisy devices or environments (80 dB or more).

Some improvements have been made in the field. Examples of references related to the present invention are described below in their own words, and the supporting teachings of each reference are incorporated by reference herein:

U.S. Pat. No. 5,475,449, issued to Pyle, discloses a device which removeably secures a standard set of earplugs to a pair of eyeglasses, preferably safety glasses, by double looping a standard cord with a pair of cord adjusters. A pair of double looped elastomeric temple securing means hold both a loop of the cord through one of each of their loops and an eyeglass temple piece through the other of their loops. The tips of the cord are provided with an annular binding surface which may be inserted into the end of a standard earplug cavity which is cylindrical in configuration and which secures the earplug to the cord tip by frictional engagement therewith.

U.S. Pat. No. 5,781,272, issued to Bright et al., discloses an eyesight and hearing safety apparatus for use by a human being. The apparatus comprises a front guard portion including a front transparent panel for protecting the eyesight of the human being. The apparatus further comprises a first and a second earplug for protecting the hearing of the human being. The apparatus further comprises a first temple having a first attachment end and a first support end. The first attachment end is hingedly attached to one end of the front guard portion. The first earplug is attached to the first temple adjacent the first support end. The first temple and the first earplug support the front guard portion from a respective auditory canal when the human being is wearing the apparatus. The apparatus further comprises a second temple having a second attachment end and a second support end. The second attachment end is hingedly attached to one end of the front guard portion. The second earplug is attached to the second temple adjacent the second support end. The second temple and the second earplug support the front guard portion from a respective auditory canal when the human being is wearing the apparatus. The first and second temples may be adjustable to horizontally and vertically position the respective earplug for comfortable insertion into the respective auditory canal of the human being.

U.S. Pat. No. 8,671,949, issued to Oshima et al., discloses a headgear-earwear assembly and a method of assembling the same. The headgear-earwear assembly can include an earwear and a headgear adapted to be coupled together. The earwear can include an elongated member, such as a cord, having a length, and an earpiece coupled to the elongated member. The headgear can include a major surface and a channel oriented substantially along the major surface of the headgear. The channel can be configured to removably house at least a portion of the length of the elongated member. The method can include positioning at least a portion of the elongated member in the channel, such that at least a portion of the length of the elongated member is removably housed in the channel.

U.S. Pat. No. 7,921,468, issued to Sutton, discloses protective eyeglasses that provide hearing protection from elevated noise levels. The protective eyeglasses have safety lenses for protection of each of the eyes. Support members extend from the lenses of the eyeglasses to the ears, and have earplugs or protectors thereon which are inserted into the ears. The side support members are spring biased towards each other so that the side members provide pressure to hold the plugs in the ears of the wearer. Ear plugs are mounted so as to swivel relative to the side support members. The side support members are telescoping and are adjustable in length.

The inventions heretofore known suffer from a number of disadvantages which include being limited in use, being limited in application, being expensive, being complex, being bulky, being cumbersome to wear, not being ergonomic, not being comfortable, not being cost-effective in implementation, restricting freedom of movement, failing to save costs by use, requiring too many steps for use, being difficult to assemble, not being universally usable with stringed earplugs, and not being comfortable when hanging safety glasses from the neck.

What is needed is a pair of safety glasses and/or a safety glasses assembly/kit that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available safety glasses. Accordingly, the present invention has been developed to provide a pair of safety glasses, a safety glasses assembly and/or kit including ear protection coupled thereto.

According to one non-limiting embodiment of the invention, there is a pair of safety glasses that may include a pair of arms that may be extending from opposite sides of an eye glass shield member. A terminal end of each of the arms, opposite the eye shield member, may include a near terminal region that may curve inwardly toward the other arm and a far terminal region further from the eye shield member than the near terminal region that curves outwardly and wherein the far terminal region may include a trap that may be defined by a hole through the far terminal region that may be in communication with a slit that may be extending from the hole to an exterior side of the far terminal region with a protrusion that may be extending into the hole, from an edge of the hole, near the slit.

The pair of safety glasses may include an earplug lanyard that may be coupled through each hole of the pair of arms. The far terminal region may be flat. The far terminal region may curve downwardly. The slit may be through a top of the far terminal region. The protrusion may extend downwardly. The far terminal region may be substantially orthogonal to the near terminal region. The hole diameter may be smaller than the diameter of the earplug lanyard. The hole diameter may be substantially larger than the diameter of the earplug lanyard such that the lanyard moves freely therethrough.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

Figure 1:
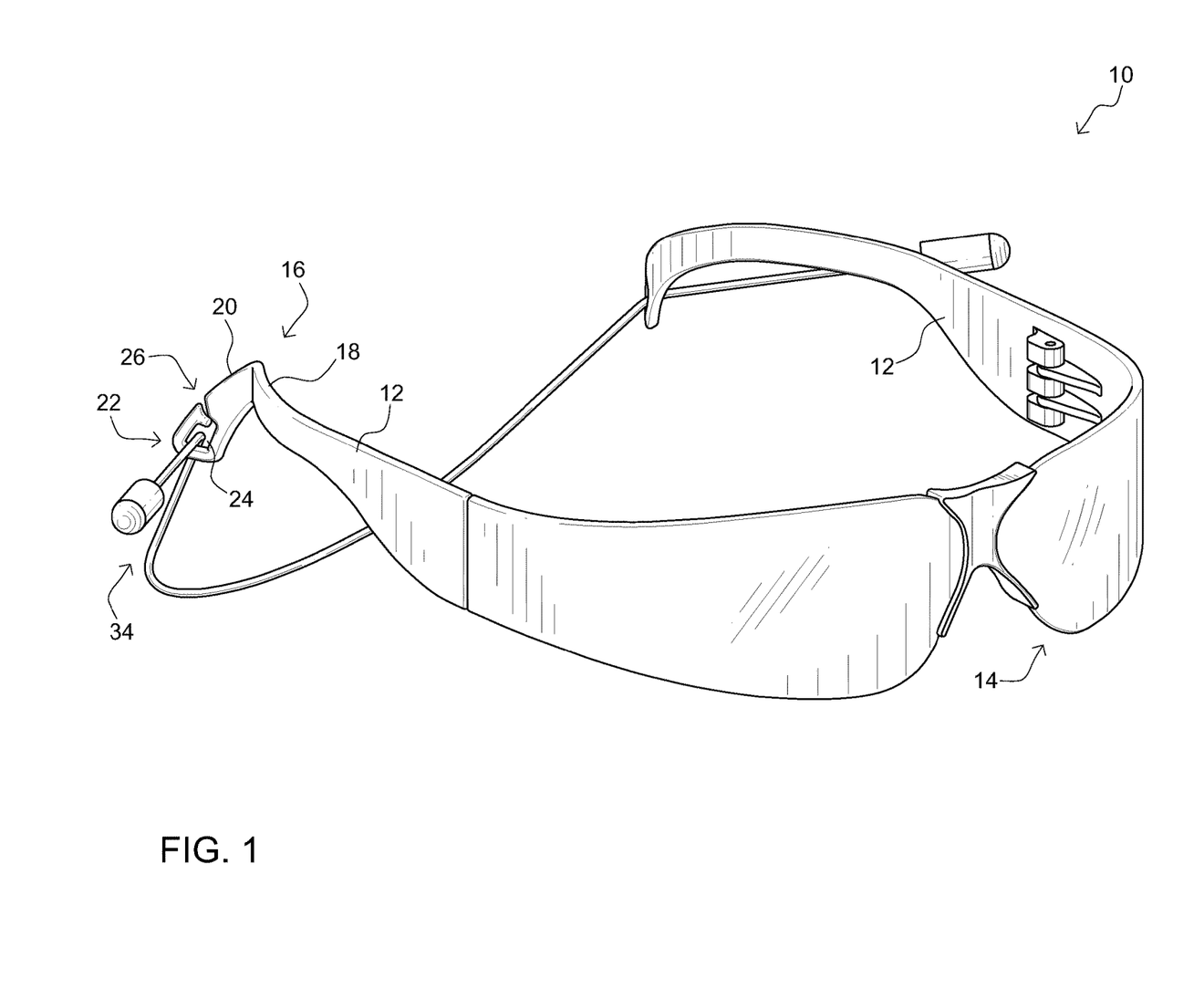
FIG. 1 is a perspective view of a pair of safety glasses, according to one non-limiting embodiment of the invention.

FIG. 1 is a perspective view of a pair of safety glasses, according to one non-limiting embodiment of the invention. There is shown a pair of safety glasses 10 including a glass shield member 14 and a pair of arms 12 with an earplug lanyard 34 disposed through the far ends thereof. Advantageously, the safety glasses 10 provide a convenient deployment of both ear and eye safety in a manner that is convenient and simple to use. Further, the risk of losing one or the other (glasses or earplugs) is reduced as the two are coupled to each other and may be conveniently stored about the neck of the user. Still more, the structures described herein and interoperation of the same provide enhanced comfort, ease of use, convenience, and safety during and after use of the same that is much improved over existing safety glasses.

The illustrated pair of safety glasses 10 includes a pair of arms 12 extending from opposite sides of an eye glass shield member 14. A terminal end 16 of each of the arms 12, opposite the eye shield member 14, includes a near terminal region 18 curving inwardly toward the other arm. The pair of arms 12 includes a far terminal region 20, further from the eye shield member 14 than the near terminal region 18, curves outwardly from the arm. The far terminal region 20 includes a trap 22 defined by a hole 24, through the far terminal region 20, in communication with a slit 26 extending from the hole 24 to an exterior side of the far terminal region 20. The trap 22 includes a protrusion 30 (See FIGS. 5 and 6) extending into the hole 24, from an edge of the hole, near the slit 26.

The illustrated pair of safety glasses 10 includes an earplug lanyard 34 coupled through each hole 24 of the pair of arms 12. The far terminal region 20 is flat. The far terminal region 20 curves downwardly. The slit 26 is through a top of the far terminal region 20. The protrusion 30 extends downwardly from the top of the far terminal region 20. The far terminal region 20 is substantially orthogonal to the near terminal region (See element 19, identifying the interior angle between the far terminal region 20 and the near terminal region 18 of FIG. 4). 18.

According to one non-limiting embodiment of the invention, there is a pair of safety glasses that incorporates hearing protection with sight protection, all-in-one. The pair of safety glasses may provide significant cost savings, in regards to loss of safety glasses and loss of earplugs. Since the earplug lanyard 34 holds the glasses 10 around a neck of a wearer when not in use and the glasses 10 may be used with any stringed hearing protection. The pair of safety glasses 10 may be O.S.H.A. approved safety glasses with a loop 34 at the end 20 of the pair of arms 12 to insert the earplug lanyard 34.

According to one non-limiting embodiment of the invention, there is a pair of safety glasses that includes a single loop 22 extending orthogonally away from each arm 12 of a pair of safety glasses 10, at a position that is slightly behind the ear of a wearer. The earplugs are fixedly coupled to a lanyard, one earplug at each end. The lanyard is disposed through each of the loops such that each earplug is disposed on either side of the head and behind of the ear.

According to one non-limiting embodiment of the invention, there is a pair of safety glasses incorporating any stringed earplugs, such as an earplug lanyard, into the safety glasses 10. The pair of earplugs may be customized earplugs such as but not limited to wherein the earplugs are detachable from the string or lanyard, so that a wearer may detach the earplugs from the string or lanyard and then may run the string or lanyard through the loop or trap, and thereby providing reusable components of the pair of safety glasses 10. The lanyard may be detachable from the earplugs and/or may include a breakaway structure to allow for selectable coupling between the lanyard and one or more of the associated earplugs. The lanyard may be a ribbon, cord, chain, string, woven fibers, plastic fiber, or the like or combinations thereof.

According to one non-limiting embodiment of the invention, the trap 22 may be tilted on an angle with respect to the plane of the arm or with respect to the long axis of the arm. Such may be from back to front (i.e. front higher and back lower, like a ramp from back to front) about 45 degrees or less. It may be that the trap is not tilted from front to back. It may be that the trap is tilted as if hinged at the connection with the ear arm plus or minus about 15 degrees.

The illustrated slit 26 in the side of the trap 22 allows a wearer to put the earplug lanyard into the trap 22 without having to run the end of the earplug therethrough. The trap 22 may be of a material that is more pliable than the arm (e.g. very pliable rubbers, plastics, gums, resins such as but not limited to neoprene, silicone, and the like and combinations thereof), which will generally include a rigid plastic, rubber or metal configured to hold its shape under pressure.

According to one non-limiting embodiment, the earplug lanyard includes one or more audio speakers, such as but not limited to one or more headphone/earbud units, which may be in conjunction with earplug structures (e.g. foam) or may replace the same. In one non-limiting embodiment the earplug lanyard is not an earplug lanyard but instead an earbud lanyard that allows the user to listen to audio.

Figure 2:
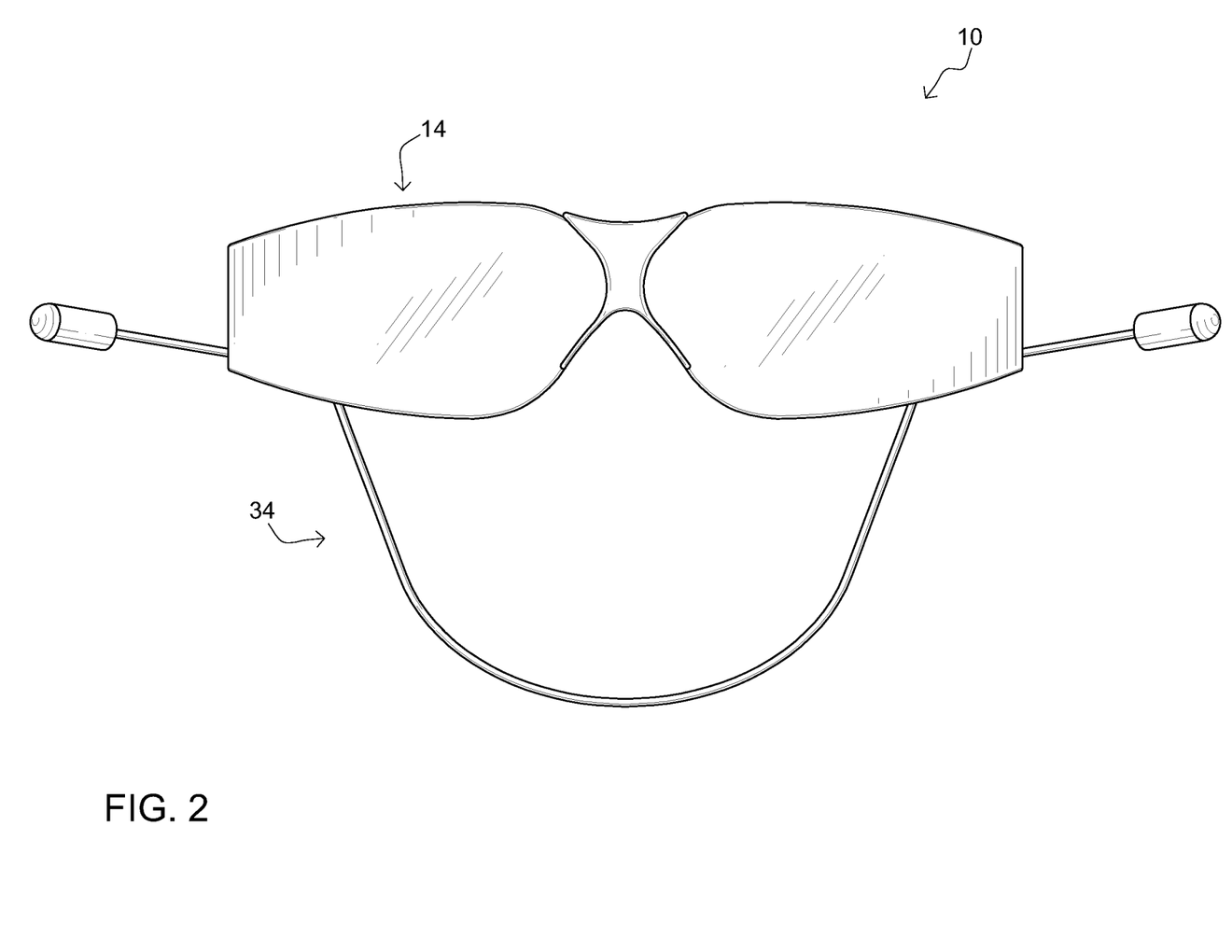
FIG. 2 is a front elevational view of a pair of safety glasses, according to one non-limiting embodiment of the invention.

FIG. 2 is a front elevational view of a pair of safety glasses, according to one non-limiting embodiment of the invention. There is shown a pair of safety glasses 10 including an eye glass shield member 14 and an earplug lanyard 34.

The illustrated pair of safety glasses 10 includes an eye glass shield member 14. The eye glass shield member 14 may include various types of glass or lens disposed therein depending on the type of work performed when being worn. The lens may vary in size, shape, tint, shade, reflection, thickness, strength, glare, etc. and still perform its intended function.

The illustrated pair of safety glasses 10 includes an earplug lanyard 34 coupled to the safety glasses, wherein the earplug lanyard may vary in length, lanyard diameter, lanyard strength, etc. and still perform its intended function. The earplug is coupled to each end of the lanyard and may vary in size, shape, material, diameter, noise canceling capabilities, etc. and still perform its intended function.

Figure 3:
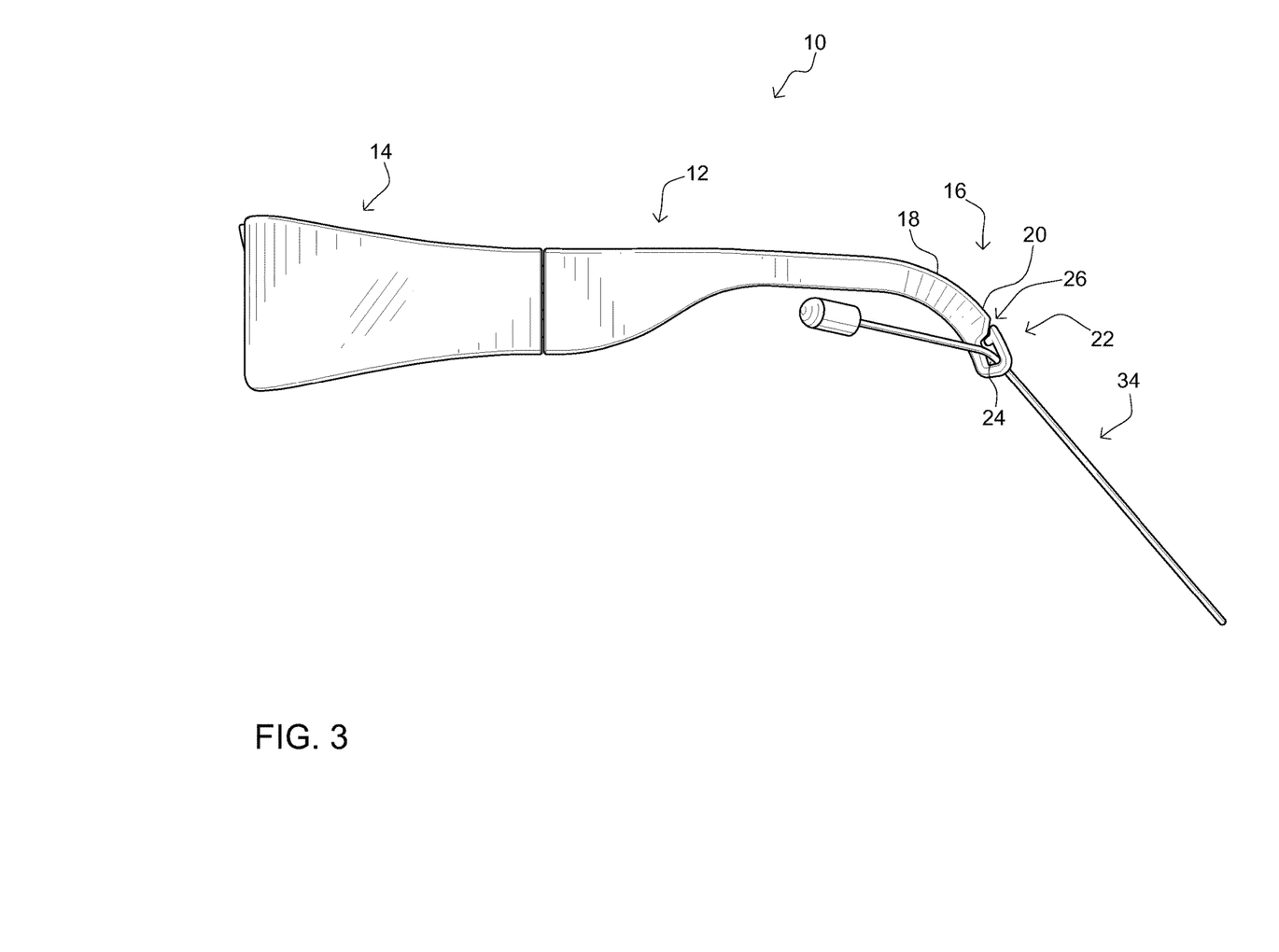
FIG. 3 is a side elevational view of a pair of safety glasses, according to one non-limiting embodiment of the invention.

FIG. 3 is a side elevational view of a pair of safety glasses, according to one non-limiting embodiment of the invention. There is shown a pair of safety glasses 10 including an arm 12 having a trap 22 and an earplug lanyard 34 coupled through the trap 22.

The illustrated pair of safety glasses 10 includes a pair of arms, but only showing one of the arms 12 extending from opposite side of an eye glass shield member 14. A terminal end 16 of each of the arm 12, opposite the eye shield member 14, includes a near terminal region 18 curving inwardly toward the other arm. The arm 12 includes a far terminal region 20, further from the eye shield member 14 than the near terminal region 18, curves outwardly from the arm 12. The far terminal region 20 includes a trap 22 defined by a hole 24, through the far terminal region 20, in communication with a slit 26 extending from the hole 24 to an exterior side of the far terminal region 20.

The illustrated pair of safety glasses 10 includes an earplug lanyard 34 coupled through the hole 24 of the arm 12. The far terminal region 20 curves downwardly. The slit 26 is through a top of the far terminal region 20. The far terminal region 20 is substantially orthogonal to the near terminal region 18. The hole diameter is smaller than the diameter of the earplug lanyard 34. The hole diameter is substantially larger than the diameter of the earplug lanyard 34 such that the lanyard 34 moves freely therethrough.

Figure 4:
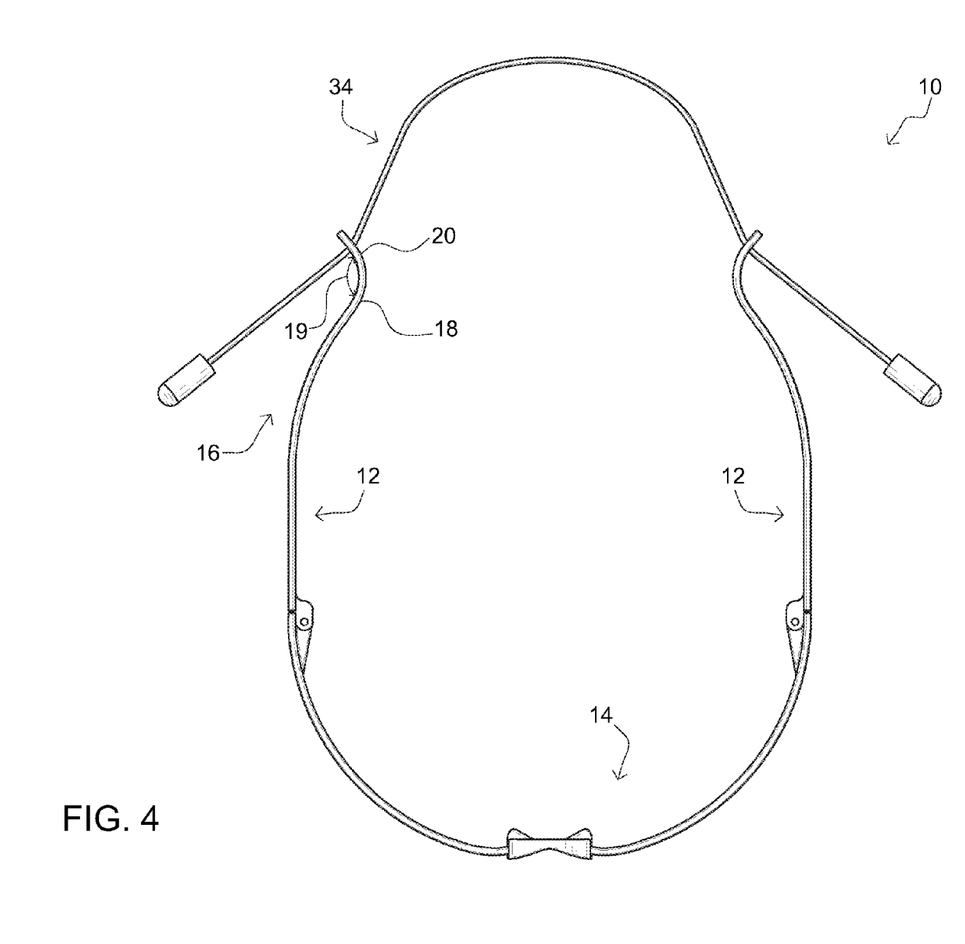
FIG. 4 is a top plan view of a pair of safety glasses, according to one non-limiting embodiment of the invention.

FIG. 4 is a top plan view of a pair of safety glasses, according to one non-limiting embodiment of the invention. There is shown a pair of safety glasses 10 including a pair of arms 12, an eye glass shield member 14, and an earplug lanyard 34 selectably coupleable to the pairs of arms 12.

The illustrated pair of safety glasses 10 includes a pair of arms 12 extending from opposite sides of an eye glass shield member 14. A terminal end 16 of each of the arms 12, opposite the eye shield member 14, includes a near terminal region 18 curving inwardly toward the other arm. The pair of arms 12 includes a far terminal region 20, further from the eye shield member 14 than the near terminal region 18, curves outwardly from the arm. The illustrated interior angle between the far terminal region and the near terminal region is less than 120 degrees. The pair of safety glasses 10 includes an earplug 34 coupled to the pair of arms 12.

The illustrated earplug lanyard 34 and the pair of safety glasses 10 completes a full circle, fully surrounding a neck or head of a wearer thereby securing the safety glasses around the wearer during use and when not in use. The earplug lanyard 34 is configured to rest upon a neck of a wearer when not in use, thereby providing a safe storage of the safety glasses 10 when not in use. The earplugs are configured to act as a stop device, so as to couple to the pair of arms when fully lengthened, thereby securing the safety glasses 10 around a neck of a wearer.

Figure 5:
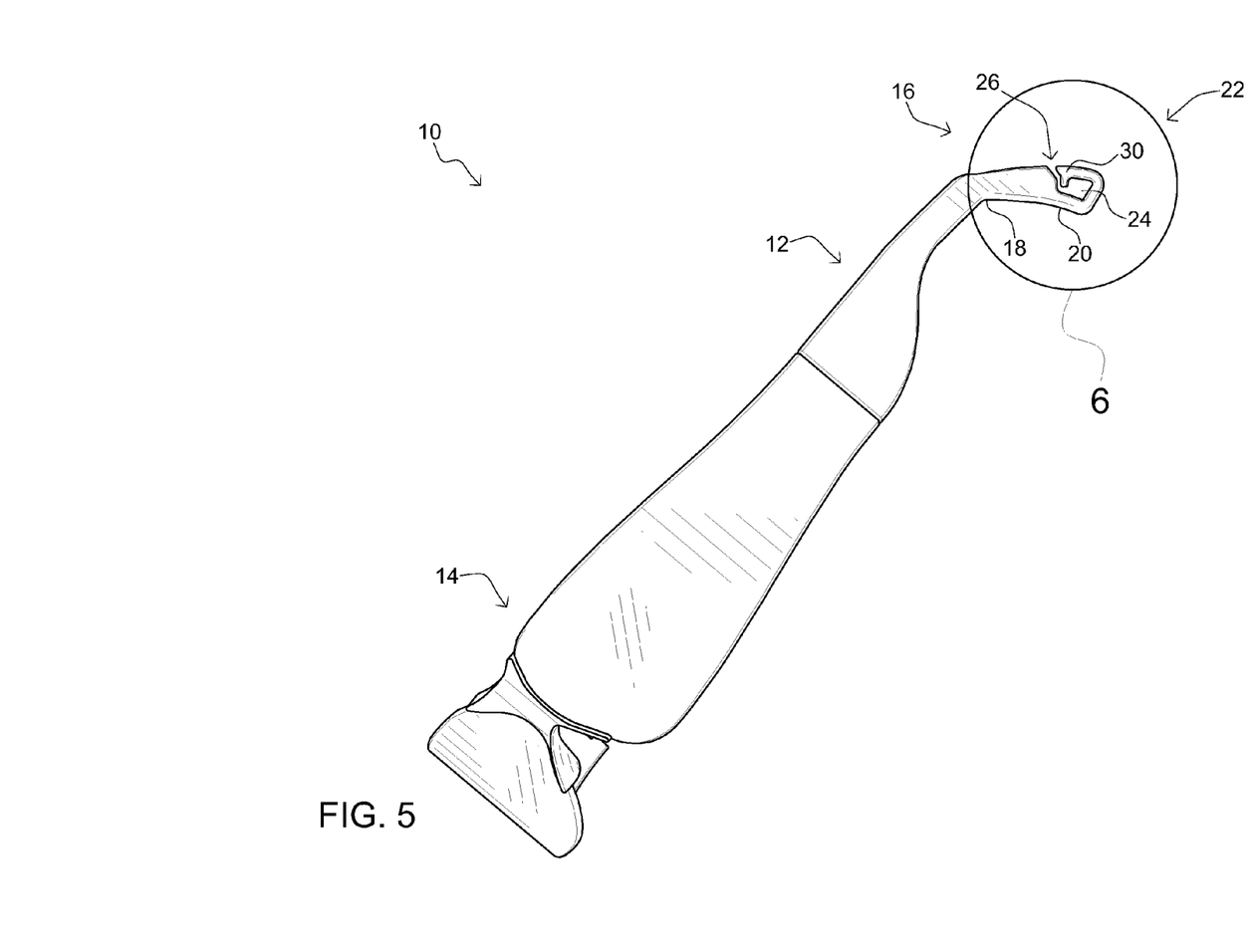
FIG. 5 is a side perspective view of a pair of safety glasses, according to one non-limiting embodiment of the invention.

FIG. 5 is a side perspective view of a pair of safety glasses, according to one non-limiting embodiment of the invention. There is shown a pair of safety glasses 10 including an eye glass shield member 14, and an arm 12 having a trap 22 disposed at an end thereof.

The illustrated pair of safety glasses 10 includes a pair of arms, but is only showing one of the arms 12 extending from opposite sides of an eye glass shield member 14. The illustrated eye glass shield member 14 includes a nose support member for supporting a nose. A terminal end 16 of each of the arms 12, opposite the eye shield member 14, includes a near terminal region 18 curving inwardly toward the other arm. The pair of arms 12 includes a far terminal region 20, further from the eye shield member 14 than the near terminal region 18, curves outwardly from the arm. The far terminal region 20 includes a trap 22 defined by a hole 24, through the far terminal region 20, in communication with a slit 26 extending from the hole 24 to an exterior side 28 of the far terminal region 20. The trap 22 includes a protrusion 30 extending into the hole 24, from an edge of the hole, near the slit 26. The far terminal region 20 is flat. The far terminal region 20 curves downwardly. The slit 26 is through a top of the far terminal region 20. The protrusion 30 extends downwardly from the top of the far terminal region 20. The far terminal region 20 is substantially orthogonal to the near terminal region 18.

Figure 6:
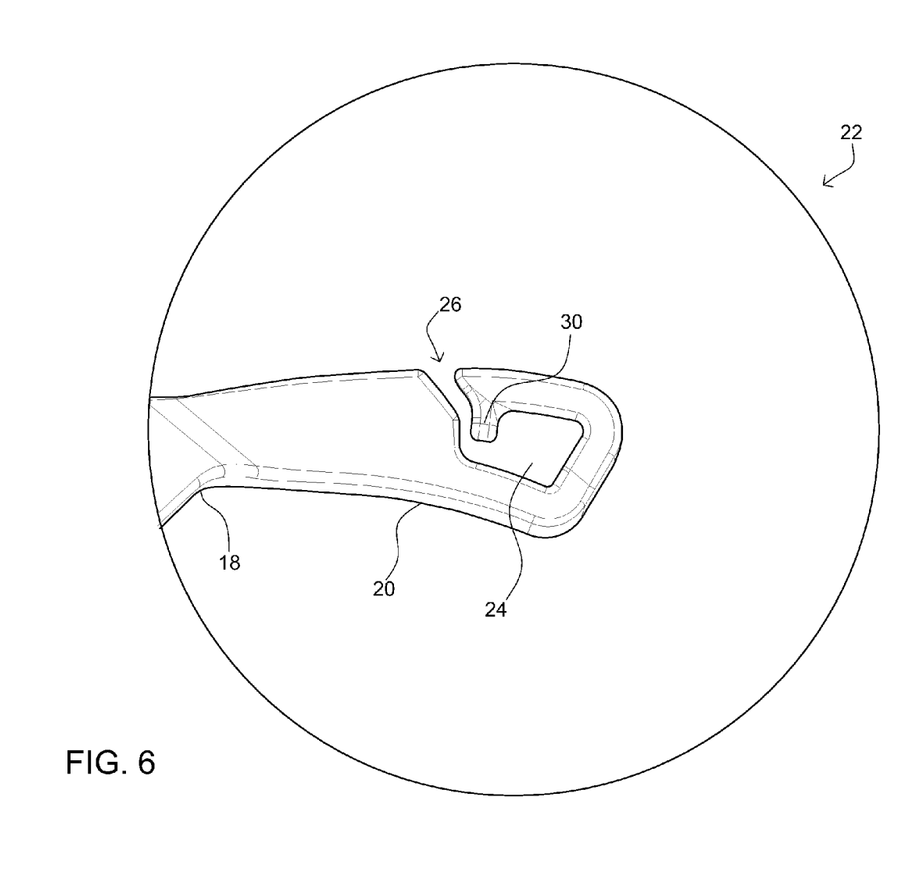
FIG. 6 is a close-up of a trap of a pair of safety glasses, according to one non-limiting embodiment of the invention.

FIG. 6 is a close-up of a trap of a pair of safety glasses, according to one non-limiting embodiment of the invention. There is shown a trap 22 of a pair of safety glasses including a hole 24, a protrusion 30, and a slit 26.

The pair of safety glasses includes a pair of arms, but FIG. 6 is only showing an end of one of the arms includes a near terminal region 18 curving inwardly toward the other arm. The arm includes a far terminal region 20, further from an eye shield member than the near terminal region 18, curves outwardly from the arm. The far terminal region 20 includes a trap 22 defined by a hole 24, through the far terminal region 20, in communication with a slit 26 extending from the hole 24 to an exterior side 28 of the far terminal region 20. The trap 22 includes a protrusion 30 extending into the hole 24, from an edge of the hole, near the slit 26. The far terminal region 20 is flat. The far terminal region 20 curves downwardly. The slit 26 is through a top of the far terminal region 20. The protrusion 30 extends downwardly from the top of the far terminal region 20. The far terminal region 20 is substantially orthogonal to the near terminal region 18. The illustrated protrusion is a fixed protrusion. The illustrated slit 26 is bounded by a terminal end of an end length of the hook-shaped trap and a first edge of the far terminal region with the protrusion being adjacent the terminal end of the hook-shaped trap and thereby elongating the slit, the protrusion being unitary with the end length of the far terminal region and having a fixed orientation orthogonal thereto.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

It is expected that there could be numerous variations of the design of this invention. An example is that the face shield of the safety glasses may cover more or less of the face of the wearer than those illustrated.

Finally, it is envisioned that the components of the device may be constructed of a variety of materials, including but not limited to rubbers, plastics, metals, ceramics, glass, minerals, woven fibers, composites, and the like and combinations thereof.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A pair of safety glasses, comprising a pair of arms extending from opposite sides of an eye glass shield member; wherein a terminal end of each of the arms, opposite the eye shield member, includes a near terminal region that curves inwardly toward the other arm and a rigid far terminal region further from the eye shield member than the near terminal region that rigidly curves outwardly and wherein the far terminal region includes a hook-shaped trap defined by a hole through the far terminal region in communication with a slit extending from the hole to an exterior side of the far terminal region the slit bounded by a terminal end of an end length of the hook-shaped trap and a first edge of the far terminal region, with a protrusion inside the hook-shaped trap extending into the hole, adjacent the terminal end of the hook-shaped trap and thereby elongating the slit, the protrusion being unitary with the end length of the hooked-shaped trap and having a fixed orientation orthogonal thereto.

2. The glasses of claim 1, further comprising an earplug lanyard coupled through each hole of the pair of arms.

3. The glasses of claim 1, wherein the far terminal region is smooth.

4. The glasses of claim 1, wherein the far terminal region curves downwardly.

5. The glasses of claim 1, wherein the slit is through a top of the far terminal region.

6. The glasses of claim 1, wherein the protrusion extends downwardly.

7. The glasses of claim 1, wherein an interior angle between the far terminal region and the near terminal region is less than 120 degrees.

8. The glasses of claim 2, wherein the hole diameter is smaller than the diameter of an earplug of the earplug lanyard.

9. The glasses of claim 2, wherein the hole diameter is larger than the diameter of the earplug lanyard such that the lanyard moves freely therethrough.

10. A pair of safety glasses, comprising:
  a) a pair of arms extending from opposite sides of an eye glass shield member; wherein a terminal end of each of the arms, opposite the eye shield member, includes a near terminal region that curves inwardly toward the other arm and a far terminal region further from the eye shield member than the near terminal region that curves outwardly and wherein the far terminal region includes a trap defined by a hole through the far terminal region in communication with a slit extending from the hole to an exterior side of the far terminal region the slit bounded by a terminal end of an end length of the hook-shaped trap and a first edge of the far terminal region, with a protrusion inside the trap and extending into the hole adjacent the terminal end of the hook-shaped tray and thereby elongating the slit, the protrusion being unitary with the end length of the hook-shaped trap and having a fixed orientation orthogonal thereto; and
  b) an earplug lanyard coupled through each hole of the pair of arms.

11. The glasses of claim 10, wherein the far terminal region is smooth.

12. The glasses of claim 11, wherein the far terminal region curves downwardly.

13. The glasses of claim 12, wherein the slit is through a top of the far terminal region.

14. The glasses of claim 13, wherein the protrusion extends downwardly.

15. The glasses of claim 14, wherein the far terminal region is orthogonal to the near terminal region.

16. The glasses of claim 15, wherein the hole diameter is smaller than the diameter of an earplug of the earplug lanyard.

17. The glasses of claim 16, wherein the hole diameter is larger than the diameter of the earplug lanyard such that the lanyard moves freely therethrough.

18. A safety glasses assembly, comprising:
  a) a pair of arms extending from opposite sides of an eye glass shield member; Wherein a terminal end of each of the arms, opposite the eye shield member, includes a near terminal region that curves inwardly toward the other arm and a rigid far terminal region further from the eye shield member than the near terminal region that curves outwardly and wherein the far terminal region includes a trap defined by a hole through the far terminal region in communication with a slit extending from the hole to an exterior side of the far terminal region the slit bounded by a terminal end of an end length of the hook-shaped trap and a first edge of the far terminal region, with a fixed protrusion, wholly inside the hole, extending into the hole, adjacent the terminal end of the hook-shaped trap and thereby elongating the slit, the protrusion being unitary with the end length of the hook-shaped trap and having a fixed orientation orthogonal thereto; and
  b) an earplug lanyard coupled through each hole of the pair of arms; wherein the far terminal region curves downwardly; wherein the slit is through a top of the far terminal region; wherein the protrusion extends downwardly; wherein the hole diameter is larger than the diameter of the earplug lanyard such that the lanyard moves freely therethrough.

* * * * *